United States Patent
Gately

(10) Patent No.: US 6,465,667 B2
(45) Date of Patent: Oct. 15, 2002

(54) SYNTHESIS AND ISOMERIZATION OF 1,2-BIS (INDENYL) ETHANES

(75) Inventor: Daniel A. Gately, Berthoud, CO (US)

(73) Assignee: Boulder Scientific Company, Mead, CO (US)

(*) Notice: Subject to any disclaimer, the term of this patent is extended or adjusted under 35 U.S.C. 154(b) by 0 days.

(21) Appl. No.: 10/075,524

(22) Filed: Feb. 14, 2002

(65) Prior Publication Data

US 2002/0099231 A1 Jul. 25, 2002

Related U.S. Application Data

(62) Division of application No. 09/912,926, filed on Jul. 25, 2001, which is a division of application No. 09/234,481, filed on Jan. 21, 1999.

(51) Int. Cl.⁷ ............................... C07F 7/00; C07F 7/28
(52) U.S. Cl. ........................................................ 556/53
(58) Field of Search .......................................... 556/53

(56) References Cited

U.S. PATENT DOCUMENTS 6,319,874 B1 * 11/2001 Winter et al. ................. 556/53

* cited by examiner

*Primary Examiner*—Paul F. Shaver
(74) *Attorney, Agent, or Firm*—Edward S. Irons

(57) ABSTRACT

A method for producing 1,2-bis(indenyl)ethanes in good yield is described. An agent and its application for isomerizing kinetic EBI to thermodynamic EBI and for isomerizing meso TMS-EBI to rac TMS-EBI are exemplified.

2 Claims, No Drawings

SYNTHESIS AND ISOMERIZATION OF 1,2-BIS (INDENYL) ETHANES

This application is a division of Ser. No. 09/912,926 filed Jul. 25, 2001, which in turn is a division of Ser. No. 09/234,481 filed Jan. 21, 1999.

FIELD OF INVENTION

This invention relates to the synthesis and isomerization of 1,2-bis(indenyl)ethanes (EBI).

BACKGROUND OF THE INVENTION

In this specification, the expression 1,2-bis(indenyl)ethane or EBI means collectively all isomers of Formula I:

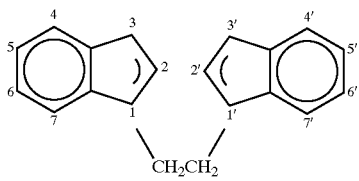

in which the symbol "(" indicates a 1,2-bis(indenyl-1)ethane which has a 1,2, 1,2' double bond (thermodynamic EBI, BRN No. 3055002, CAS RN No. 18657-57-3) or a 2,3 2',3' double bond (kinetic EBI, BRN No. 3083835, CAS RN Nos. 15721-07-0, 18686-04-9, 18686-05-0). The two unnumbered fusion C atoms are asymmetric. The 1,1'C atoms are asymmetric in kinetic EBI compounds. The 3,3' C atoms are asymmetric when substituted.

Each of the ring substituents may be hydrogen or any one to ten carbon atom hydrocarbyl group. Each ring substituent may be the same as or different from any other ring substituent. One to ten carbon atom alkyl groups are preferred. 2,2' methyl and 4,7, 4'7' dimethyl EBIs are representative.

The EBI 3,3' substituents may be any hydrocarbyl group or hydrocarbyl silyl group, preferably having one to ten carbon atoms. Useful alkyl silyl 3,3' substituents have the formula $(R)_3$—Si, in which R is a one to ten carbon atom hydrocarbyl group, typically an alkyl group. The methyl group is preferred. Each R may be the same as or different from each of the other two R groups. Chiral TMS-EBI is preferred.

Meso and rac (racemic) forms of kinetic EBI and thermal isomerization of kinetic to thermodynamic EBI are known phenomena. Maréchal, et al, *Bulletin de la Societe Chimique de France* (1967) 8:2954–2961.

Kinetic and thermodynamic EBI are interchangeably useful separately and in mixtures as ligands for metallocene olefin polymerization catalysts. However, the large-scale production of kinetic EBI is constrained because the thermodynamic isomer is produced at temperatures below about −70° C.; whereas, at higher temperatures low yields of kinetic EBI consequent from spiro indene and vinylidene impurities may result. See, e.g., Yang, et al., *SYNLETT* (1996) 147 and Collins, et al., *J.Organometallic Chem.* (1988) 342:21 (thermodynamic EBI synthesized at −78° C. stirred overnight and warmed to room temperature). See also, Ewen, J., et al., *J.Am.Chem.Soc.* (1987) 109:6544–6545 and Grossman, R., et al., *Organometallics* (1991) 10:1501–1505 (50% to 80% recrystallized yields of thermodynamic isomer because of the formation of spiroindene by-product).

3,3' C. substitution imparts chirality to some Formula I compounds with consequent achiral meso and chiral racemic forms. Metallocene isotactic polypropylene catalysts may require substantially pure rac EBI ligands; for example, rac 1,2-bis(3,3'trimethylsilyl indenyl-1)ethane (hereinafter rac TMS-EBI). Typically, TMS-EBI may be produced by reaction of EBI with two equivalents of BuLi to produce dilithio EBI. Dilithio EBI is treated with two equivalents of TMSC1 to produce 3,3'-bis TMS-EBI. Synthesis of substituted EBI compounds, including TMS-EBI, typically yields a mixture of meso and rac forms. Separation of the rac form from such mixtures may not be practical for industrial applications.

SUMMARY OF THE INVENTION

The invention may comprise a method for producing EBI from an indene in good yield at moderate temperatures.

Pursuant to one aspect of the invention, a method is provided for the moderate temperature synthesis of kinetic EBI substantially free of by-product impurities.

Important embodiments of the invention include isomerization agents effective to convert kinetic EBI to thermodynamic EBI and also to convert meso 3,3' substituted EBI to a meso/rac mixture. The invention may include isomerization protocols implemented by these reagents.

The invention may include a series of moderate temperature steps to produce a reaction mixture from which solid kinetic EBI which may be substantially free of spiro indene impurities is separated from a mother liquor. The solid kinetic EBI may be separated in a single increment or in a plurality of increments, each of said increments being separated from the mother liquor of the preceding increment. Each mother liquor may comprise a solution of additional kinetic EBI which may be isomerized to thermodynamic EBI, preferably in solution in its mother liquor which is cooled induce precipitation of solid thermodynamic EBI. The solid kinetic and thermodynamic EBI products are useful separately or in combination as metallocene catalyst ligands. This procedure for synthesizing thermodynamic EBI, which includes an isomerization step, is practiced and scalable, and is an improvement over the lower yielding preparation of thermodynamic EBI which requires starting the reactions at temperatures below −70° C. reported in the cited references.

The invention may include isomerization of a meso 3,3' substituted EBI, such as TMS-EBI to yield a meso and rac mixture. Treatment of an existing mixture of meso and rac 3,3' substituted EBI with the isomerization agent yields a product mixture enriched in the rac isomer. The stereospecific transformation of racemic TMS-EBI to racemic metallocene is known. See, e g., Nifant'ev, I. A., et al. (1997) *Organometallics* 16:713–715. However, racemic TMS-EBI was isolated in only 34% crystallized yield from the reaction of dilithio EBI and a trimethyl silicon chloride. The isomerization of meso to meso-rac TMS pursuant to this invention is an improvement over the prior art because racemic TMS-EBI is used to synthesize racemic metallocene. Iteration of the isomerization reaction with rac enrichment of the product mixture at each iteration may yield an ultimate substantially pure, e.g., 96% pure, rac product useful as a stereospecific metallocene olefin polymerization catalyst ligand.

DETAILED DESCRIPTION OF THE INVENTION

1. Synthesis of EBI

Formula I EBIs produced by any of the several known methods may be used in any one or more of the embodiments of the invention.

2. The Isomerization Agents

The isomerization agents useful in this invention are solutions of alkali metal alkoxides having the formula MOR, wherein M is any alkali metal and R is as defined. In the preferred isomerization agents, R is t-butyl.

Useful isomerization agents are alkali metal alkoxide solutions in a non-interfering, preferably ether, solvent. Suitable solvents include tetrahydrofuran, 2-methyl tetrahydrofuran, dioxane, and 1,2-dimethoxyethane. The isomerization agent solution may contain any functional concentration, e.g., from 10 mol percent to 20 mol percent, of alkali metal alkoxide. The preferred isomerization agent is a 10 to 20 mol percent solution of potassium tertiary butoxide in tetrahydrofuran.

3. The Isomerization Reactions

The isomerization reagents convert kinetic EBI to thermodynamic EBI. They also convert meso 3,3'-substituted chiral EBI to a mixture of the meso and rac forms.

In general, the isomerization reaction is accomplished by treatment of a kinetic EBI or meso 3,3'-substituted EBI with the isomerization reagent under conditions and for a time effective to accomplish the desired reaction. Selection of the appropriate conditions for a particular isomerization is determined by the skilled man as a function of the particular isomerization involved and of the degree of conversion desired. It is known that by going from sodium methoxide to potassium t-butoxide, a substantial increase in basic strength as well as more favorable solubility in ether is achieved. See, Gilman (1953) *Organic Chemistry* Vol. III, pp. 4–5, citing Gould, Jr., et al. (1935) *J.Am.Chem.Soc.* 57:340, and Renfrow (1944) *J.Am.Chem.Soc.* 66:144.

Each type of isomerization may be accomplished to some degree by treatment of the particular EBI isomer with an isomerization reagent at a temperature of from about 20° C. to reflux for a time period of 30 minutes to 12 hours. The kinetic to thermodynamic EBI isomerization appears to be facilitated by a higher temperature and a longer time than the 3,3'-bis TMS-EBI meso to meso:rac mixture isomerization. For example, 100% conversion of kinetic to thermodynamic EBI may be accomplished by overnight reflux in the reagent solvent such as THF. Less than 100% isomerization occurs at lower temperatures or in a shorter reflux time. In contrast, 100% meso TMS-EBI is converted in 30 minutes at room temperature (20° C.) by a similar isomerization agent to a 50/50 rac-meso mixture.

4. Work-UP of Kinetic EBI Reaction Mixture

This aspect of the invention relates to the recovery of kinetic EBI from a synthesis reaction mixture. An important step entails exchange of any non-hydrocarbon reaction mixture solvent for a hydrocarbon solvent from which kinetic EBI may be precipitated, e.g., by cooling with consequent crystallization. Appropriate hydrocarbon solvents are five to eight carbon atom alkanes. Hexane and commercially available mixtures of hexanes preferred. Aromatic hydrocarbon solvents including benzene, toluene, and xylene may be used having due regard to conditions requisite to crystallization from a particular solvent.

The hydrocarbon solution of kinetic EBI is cooled to cause precipitation of at least a portion of solute. The quantity of kinetic EBI precipitated is a function of the conditions imposed. The solid kinetic EBI is separated, typically by filtration, from the mother liquor solution of additional kinetic EBI. The separated solid kinetic EBI is dried. A yield of 20% to 50% from indene is typical.

5. Work-Up of Kinetic EBI Mother Liquor

This mother liquor or filtrate from the separation of solid kinetic EBI is treated with an isomerization agent as described in Sections 4 and 5, wherein the kinetic EBI solute is converted to the thermodynamic isomer. The isomerization reaction mixture is cooled or otherwise treated to induce precipitation of thermodynamic EBI. The precipitate is recovered. The combined yield of solid kinetic and thermodynamic EBI from indene may exceed 60%.

6. Conversion of EBI to a Metallocene

Either the separated kinetic EBI product of step 5, or the separated thermodynamic product of step 6, or a mixture thereof may be used in subsequent procedures to yield other products. An important aspect of this invention is the substantial combined yield of both EBI isomers from indene at relatively low reaction temperatures. The EBI product mixture is used in known manner to produce, inter alia, metallocene olefin polymerization catalysts having the formula $$A_2ZX_2$$

in which A is a mixture of kinetic and thermodynamic EBI, Z is Zr, Ti or Hf, and X is a halogen. Z is typically Zr and X is typically chlorine. $(EBI)_2ZrCl_2$ is a typical catalyst. Typically, such metallocenes are produced by the reaction of a ligand lithenide with a Group IV tetrahalide. See, generally, Spaleck (1994) *Organometallics* 13:954–963, *Journal of Orpanometallic Chem.* 288 (1985) 63–67, and various Spaleck patents, including U.S. Pat. Nos. 5,145,819 and 5,278,264.

EXEMPLIFICATION OF THE INVENTION

EXAMPLE I

Laboratory

Indene in diethyl ether (1.25 equivalents) was treated with BuLi in ethyl ether at −20° C. to provide reaction mixture containing lithium indenide pursuant to Equation 1, Equation 1

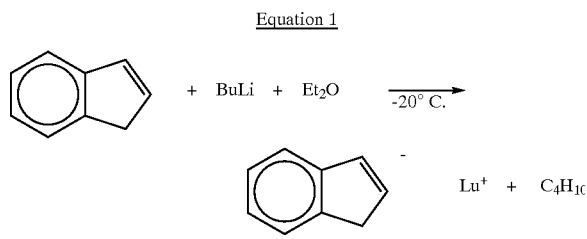

The lithium indenide containing reaction mixture was warmed to room temperature, was stirred for one hour, and then treated 0.5 mol of with dibromoethane. Ten minutes later tetrahydrofuran (THF) (0.25 equiv.) was added. The temperature of the reaction slowly warmed to 40° C.

The $^1H$ NMR of the product mixture showed >95% yield from indene of the kinetic isomer of EBI. No spiro product was observed. See Equation 2.

Equation 2

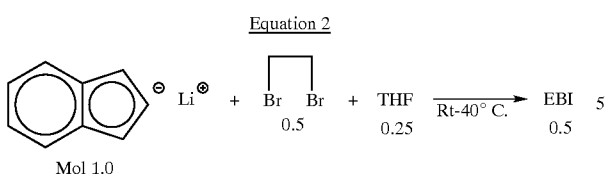

Water was added and the mixture separated into an aqueous phase and an organic phase. The organic phase was separated and dried with sodium sulfate.

The organic phase solvent (i.e., THF and hexanes) was exchanged with hexanes in an amount such that the final volume was concentrated to about 40 weight % of Kinetic EBI. The solution was cooled to −20° C. and filtered. The solid was dried to give a 35% yield of the kinetic isomer of EBI.

EXAMPLE I(a)

Laboratory

The Example I filtrate, a hexane solution of kinetic EBI, was treated with 20 mol % potassium tertiary butoxide in THF and refluxed overnight. $^1$H NMR of the reaction mixture showed 100% conversion of the kinetic EBI content to thermodynamic EBI. The isomerization is illustrated by Equation 3:

Equation 3

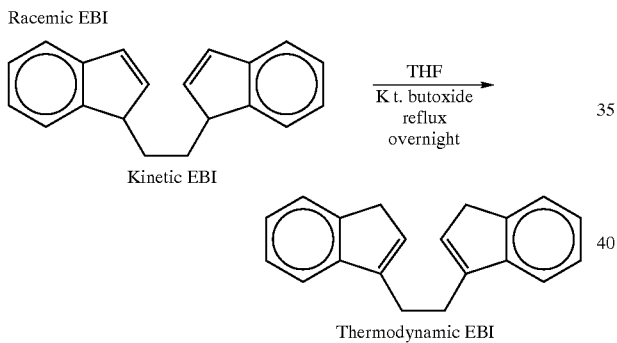

The resulting hexane solution of thermodynamic EBI was cooled to −20°. The solid thermodynamic EBI precipitated and was removed by filtration. The solid was dried to give an additional 50% of thermodynamic EBI. Total yield of from indene was 85%.

EXAMPLE II

Meso to Rac Isomerization of TMS-EBI 1.0 mol pure meso bis-1,2(3,3' TMS-EBI)ethane was dissolved in THF (403 g) and 0.2 mol potassium tertiary butoxide (KOtbu) was added in one portion to provide a THF solution containing 20 mol percent of KOtbu. The solution changed color immediately from yellow to green. The reaction mixture was stirred for 30 minutes. $^1$H NMR of the crude mixture showed rac/meso in a 50:50 ratio.

Upon addition of 3% aqueous NaCl, the reaction product separated into an organic layer and an aqueous layer. The organic layer was separated and washed with water; the THF solvent was exchanged with heptane under conditions such that a heptane solution containing about 35% bis-1,2(3,3' TMS-EBI-1) was obtained. The heptane solution was cooled to −20° C. and the meso isomer crystallized. The solid meso was separated (198 g) by filtration. The filtrate that contained rac was distilled, leaving behind a sticky semi-solid that contained 200 g of 90% diastereomerically pure rac.

EXAMPLE II(a)

The solid meso collected in Example II was converted to a 50 meso/50 rac mixture from which the rac was separated by reiteration of the Example I work-up.

EXAMPLE III

Example II is repeated using 2,2' methyl substituted TMS-EBI. An isomerization reaction mixture having a 65:35 meso:rac ratio was produced:

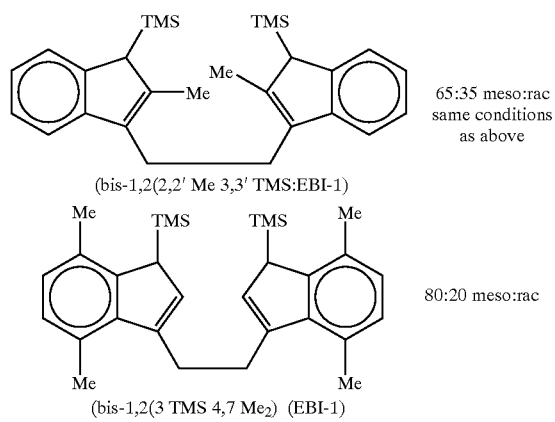

EXAMPLE IV

Laboratory

Example II is repeated using 4,4':7,7' methyl substituted TMS-EBI. An isomerization reaction mixture having an 80:20 meso:rac ratio was produced:

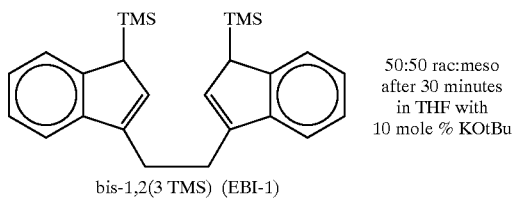

EXAMPLE V

Batch Record

Synthesis of Rac-1,2-Ethylenebis(3-trimethylsilyl-1-indenyl)ethane

Process Description 1,2-Bis(indenyl)ethane, BSC-395 and THF are charged to a reaction vessel. Butyllithium in hexanes is then added slowly. This mixture is then slowly heated to room temperature and agitated. THF and TMSCl (trimethylsilyl chloride) are added to the vessel, and the lithiated EBI is fed in cold. THF and unreacted TMSCl are distilled to the vessel. Heptane is added. The slurry is filtered through a sparkler filter, collecting lithium salts. The filtrate is cooled, and the meso product is collected on a filter. The meso ligand is treated with potassium t-butoxide to isomerize to a rac-:meso-mixture. The isomer mixture is separated.

REACTIONS

Reaction 1:

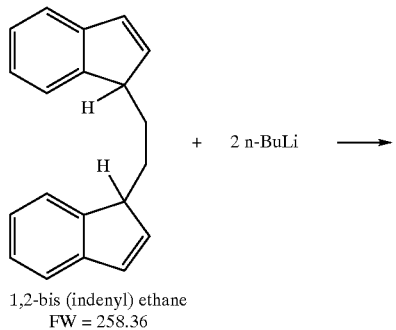

1,2-bis (indenyl) ethane
FW = 258.36

Reaction 2:

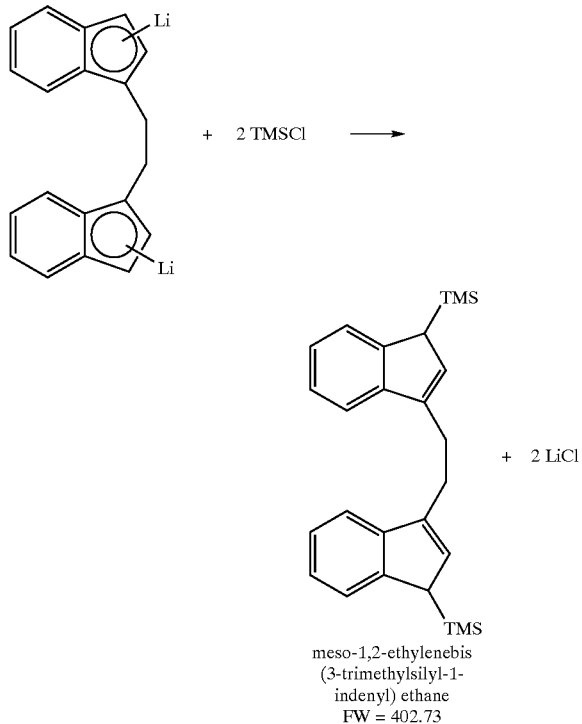

meso-1,2-ethylenebis
(3-trimethylsilyl-1-
indenyl) ethane
FW = 402.73

Reaction 3

Meso product of reaction 2 is treated with potassium t-butoxide in THF. Product of Reaction 3—50/50 rac and meso 1,2-ethylenebis(3-trimethylsilyl-1-indenyl)ethane.

(i) Exemplification of Reaction 1

A nitrogen purged first reactor [190–241] was charged with 9.1 kgs of 1,2-bis(indenyl)ethane. 90.7 kgs of THF is charged to the first reactor vessel. Thereafter, the pot temperature of the first reactor vessel is reduced to the range of −25° C. to −20° C. under 2–5 psig regulated nitrogen.

29.9 kgs of 1.6 molar n-butyl lithium in hexane is fed to first reactor vessel at a rate effective to maintain the pot temperature in the range of −25° C. to −15° C. Upon completion of n-butyl lithium addition, the pot temperature of the first reactor is raised to a temperature of 20° C. to 25° C. over a time period of 16 hours. The pot temperature is then raised to about 30° C. to dissolve the reactor product slurry and the contents of the first reactor vessel are transferred from the first reactor vessel to a dry, glass holding receiver ["receiver"]. The first reactor is maintained wet with THF after the transfer of its contents to the receiver.

(ii) Exemplification of Reaction 2

11.5 kgs of trimethylsilyl chloride are charged to the THF wet first reactor vessel. The pot temperature of the first reactor vessel is lowered to the range of −20° C. to −10° C. The contents of the glass holding receiver are added to the first reactor vessel over a 30 minute time period while the pot temperature is maintained in the range of −20° C. to −10° C. The resulting reaction mixture is agitated under 2–5 psig regulated nitrogen as the pot temperature is slowly raised to 20° C. to 25° C. over a period of three hours. Thereafter, the contents of the first reactor are stripped to a paste by distillation of THF and TMSCl to a temperature of 95° C.

(iii) Exemplification of Reaction 3

The neutralized distillate which comprises a solution of meso TMS is transferred to a second reactor [115-254]. 5.5 kgs of heptane is added to the second reactor at a temperature of 20° C. to 25° C. THF content of the second reactor is reduced to less than 2% by distillation of heptane/THF.

The temperature of the second reactor contents is adjusted, if necessary, to 78° C. to 82° C., and that reactor is emptied by filtration to remove lithium salts. The filtrate, a solution of meso solids, is transferred to a nitrogen purged drum. The second reactor is rinsed twice with heptane at 78° C. to 82° C. in an amount sufficient to provide a 35% solution of meso solids when combined with the filtrate form the second reactor contents.

The combined rinse heptane and the filtrate from the second reactor are transferred to the first reactor at a temperature of −30° C. to −20° C. The resulting meso solids precipitate is removed by filtration and dried.

The dry meso solids are transferred to a third reactor [95-252] which is charged with 13 kgs. of THF. 135 grams of potassium t-butoxide are added by sprinkling to the contents of the third reactor with agitation for 30 minutes. A 50:50 meso:rac mixture is produced.

The third reactor is charged with 11.3 liters of water, followed by 1.3 kgs. of sodium chloride which, in turn, is followed by 5.4 kgs. of ethyl ether. The reaction mixture is agitated for 15 minutes, and settled for 15 minutes. A lower aqueous and an upper organic layer form. The lower aqueous layer is removed. Pot temperature of the third reactor is adjusted to less than 20° C. 2 kgs. of sodium sulfate is added with agitation for two hours. The agitated mixture is allowed to settle for 20 minutes, and filtered to a dry second reactor. Solvents are distilled, the contents of the second reactor are cooled to 20° C. to −20° C., and charged with heptane in an amount sufficient to provide a 35% solution of 50:50 rac:meso solids. THF content is adjusted, if necessary, to less than 2%.

The first reactor [109-241] is cooled to −30° C. to −20° C. The resulting solids are removed by filtration and dried. The filtrate is retained for further processing.

I claim:
1. A composition of matter having the formula

$$A_2MX_2$$

wherein A is a mixture of kinetic and thermodynamic EBI, M is zirconium, titanium or hafnium, and X is a halogen.

2. The claim 1 composition of matter wherein M is zirconium and X is chlorine.

* * * * *